United States Patent
Guzik et al.

(10) Patent No.: US 11,477,616 B2
(45) Date of Patent: Oct. 18, 2022

(54) SAFETY DETECTION CONTROLLER

(71) Applicants: Getac Technology Corporation, Taipei (TW); WHP Workflow Solutions, Inc., North Charleston, SC (US)

(72) Inventors: Thomas Guzik, Edina, MN (US); Muhammad Adeel, Edina, MN (US)

(73) Assignees: Getac Technology Corporation, Taipei (TW); WHP Workflow Solutions, Inc., North Charleston, SC (US)

( * ) Notice: Subject to any disclaimer, the term of this patent is extended or adjusted under 35 U.S.C. 154(b) by 0 days.

(21) Appl. No.: 17/107,764

(22) Filed: Nov. 30, 2020

(65) Prior Publication Data
US 2022/0174454 A1    Jun. 2, 2022

(51) Int. Cl.
*H04W 4/029*    (2018.01)
*H04W 64/00*    (2009.01)
*H04W 76/14*    (2018.01)
*H04W 8/18*    (2009.01)
(Continued)

(52) U.S. Cl.
CPC ............ *H04W 4/029* (2018.02); *G16H 50/80* (2018.01); *H04L 67/306* (2013.01); *H04W 8/183* (2013.01); *H04W 64/003* (2013.01); *H04W 64/006* (2013.01); *H04W 76/14* (2018.02)

(58) Field of Classification Search
CPC ..... H04W 72/02; H04W 4/023; H04W 4/029; H04W 4/80; H04W 4/90; H04W 92/18; H04W 12/02; H04W 12/03; H04W 12/63; H04W 12/65; H04W 12/72; H04W 24/08; H04W 4/38; H04W 52/0254; H04W 64/00; H04W 72/121; H04W 84/12
See application file for complete search history.

(56) References Cited

U.S. PATENT DOCUMENTS

| | | |
|---|---|---|
| 6,760,744 B1 | 7/2004 | Halaas et al. |
| 7,917,888 B2 | 3/2011 | Chong et al. |
| 8,452,722 B2 | 5/2013 | Naeve et al. |

(Continued)

FOREIGN PATENT DOCUMENTS

| | | |
|---|---|---|
| CN | 109671266 B | 11/2020 |
| JP | 2008204219 A | 9/2008 |

(Continued)

OTHER PUBLICATIONS

U.S. Appl. No. 17/107,891, Final Office Action dated Aug. 5, 2021, 21 pages.

(Continued)

*Primary Examiner* — Kwasi Karikari
(74) *Attorney, Agent, or Firm* — Han Santos, PLLC

(57) ABSTRACT

This disclosure describes techniques that enable a safety detection controller to analyze and infer a likelihood of a safety concern impacting a monitored individual at a real-time event. More specifically, a safety detection controller may receive sensor data from a monitored device associated with a particular individual. The sensor data may be captured from the environment that is proximate to the monitored device. The safety detection controller is further configured to analyze the sensor data to infer the identities of third-party individuals proximate to the monitored device and determine whether those individuals pose a safety concern to the monitored individual.

20 Claims, 8 Drawing Sheets

(51) Int. Cl.
*G16H 50/80* (2018.01)
*H04L 67/306* (2022.01)

(56) References Cited

U.S. PATENT DOCUMENTS

| | | | |
|---|---|---|---|
| 8,606,844 B2 | 12/2013 | Kaurman et al. | |
| 8,688,320 B2 | 4/2014 | Faenger | |
| 9,110,774 B1 | 8/2015 | Bonn et al. | |
| 9,264,678 B2 | 2/2016 | Nuyttens et al. | |
| 9,449,229 B1 | 9/2016 | Laska et al. | |
| 9,483,732 B1 | 11/2016 | Milakovich | |
| 9,485,474 B2 | 11/2016 | Kim et al. | |
| 9,681,104 B2 | 6/2017 | Billau et al. | |
| 9,723,251 B2 | 8/2017 | Slotky | |
| 9,738,125 B1 | 8/2017 | Brickley et al. | |
| 9,755,890 B2 | 9/2017 | Robertson et al. | |
| 9,832,205 B2 | 11/2017 | Santhi et al. | |
| 9,848,312 B2 | 12/2017 | Sundel et al. | |
| 9,852,132 B2 | 12/2017 | Chhichhia et al. | |
| 9,886,261 B1 | 2/2018 | Hotchkies | |
| 10,324,773 B2 | 6/2019 | Wing et al. | |
| 10,460,014 B2 | 10/2019 | Lloyd et al. | |
| 10,540,883 B1 | 1/2020 | Keil et al. | |
| 10,902,955 B1* | 1/2021 | Federoff | G16H 50/30 |
| 11,238,290 B2 | 2/2022 | Burns et al. | |
| 2003/0081127 A1 | 5/2003 | Kirmuss | |
| 2003/0095688 A1 | 5/2003 | Kirmuss | |
| 2003/0163512 A1 | 8/2003 | Mikamo | |
| 2003/0208679 A1 | 11/2003 | Vazquez | |
| 2006/0257001 A1 | 11/2006 | Veen et al. | |
| 2008/0147267 A1 | 6/2008 | Plante et al. | |
| 2008/0303903 A1 | 12/2008 | Bentley et al. | |
| 2009/0150017 A1 | 6/2009 | Caminiti et al. | |
| 2009/0210455 A1 | 8/2009 | Sarkar et al. | |
| 2009/0248711 A1 | 10/2009 | Martinez et al. | |
| 2009/0284359 A1 | 11/2009 | Huang et al. | |
| 2010/0036560 A1 | 2/2010 | Wright et al. | |
| 2010/0144318 A1 | 6/2010 | Cable | |
| 2011/0205068 A1 | 8/2011 | Huynh et al. | |
| 2011/0302151 A1 | 12/2011 | Abadi et al. | |
| 2012/0084747 A1 | 4/2012 | Chakradhar et al. | |
| 2013/0039542 A1 | 2/2013 | Guzik | |
| 2013/0344856 A1 | 12/2013 | Silver et al. | |
| 2013/0347005 A1 | 12/2013 | Lam et al. | |
| 2014/0343796 A1 | 11/2014 | Abuelsaad et al. | |
| 2015/0089019 A1 | 3/2015 | Chou | |
| 2015/0341370 A1 | 11/2015 | Khan | |
| 2016/0042767 A1 | 2/2016 | Araya et al. | |
| 2016/0086397 A1 | 3/2016 | Phillips | |
| 2016/0153801 A1 | 6/2016 | Cho et al. | |
| 2016/0190859 A1 | 6/2016 | Blum et al. | |
| 2016/0248856 A1 | 8/2016 | Kao | |
| 2016/0371553 A1 | 12/2016 | Farnham, IV et al. | |
| 2016/0378607 A1 | 12/2016 | Kumar et al. | |
| 2017/0011324 A1 | 1/2017 | Truong et al. | |
| 2017/0048482 A1 | 2/2017 | Drako et al. | |
| 2017/0148027 A1 | 5/2017 | Yu et al. | |
| 2017/0161323 A1 | 6/2017 | Simitsis et al. | |
| 2017/0161409 A1 | 6/2017 | Martin | |
| 2017/0164062 A1 | 6/2017 | Abramov et al. | |
| 2018/0079413 A1 | 3/2018 | Herrero et al. | |
| 2018/0145923 A1 | 5/2018 | Chen et al. | |
| 2018/0285759 A1 | 10/2018 | Wood et al. | |
| 2018/0365909 A1 | 12/2018 | Cheng et al. | |
| 2019/0019122 A1 | 1/2019 | Allen | |
| 2019/0026665 A1 | 1/2019 | Caskey et al. | |
| 2019/0043351 A1 | 2/2019 | Yang et al. | |
| 2019/0054925 A1 | 2/2019 | Froeschl et al. | |
| 2019/0140886 A1 | 5/2019 | Zywicki et al. | |
| 2019/0325354 A1 | 10/2019 | Rajnayak et al. | |
| 2020/0007827 A1 | 1/2020 | Saad et al. | |
| 2020/0072637 A1 | 3/2020 | Guidotti et al. | |
| 2020/0074156 A1 | 3/2020 | Janumpally et al. | |
| 2020/0081899 A1 | 3/2020 | Shapur et al. | |
| 2020/0145620 A1 | 5/2020 | Alcantara et al. | |
| 2020/0151360 A1 | 5/2020 | Zavesky et al. | |
| 2020/0172112 A1 | 6/2020 | Kawashima | |
| 2020/0211216 A1 | 7/2020 | Hagio et al. | |
| 2020/0304854 A1 | 9/2020 | Baumgartner et al. | |
| 2020/0312046 A1 | 10/2020 | Righi et al. | |
| 2020/0351381 A1 | 11/2020 | Lacey et al. | |
| 2021/0076002 A1 | 3/2021 | Peters et al. | |
| 2021/0089374 A1 | 3/2021 | Watson et al. | |
| 2021/0133808 A1 | 5/2021 | Chan et al. | |
| 2021/0272702 A1* | 9/2021 | Hakami | H04W 4/029 |
| 2021/0297929 A1 | 9/2021 | Frusina et al. | |
| 2021/0377205 A1 | 12/2021 | Brown et al. | |
| 2022/0014907 A1 | 1/2022 | Boyd et al. | |
| 2022/0169258 A1 | 6/2022 | Samarthyam et al. | |

FOREIGN PATENT DOCUMENTS

| | | |
|---|---|---|
| KR | 20130010400 A | 1/2013 |
| KR | 20190086134 A | 7/2019 |
| WO | 2010056891 A1 | 5/2010 |

OTHER PUBLICATIONS

U.S. Appl. No. 17/107,891, Office Action dated Apr. 1, 2021, 22 pages.

U.S. Appl. No. 17/107,877, Office Action dated Aug. 18, 2021, 40 pages.

International Patent Application No. PCT/US2021/060890, International Search Report and Written Opinion dated Mar. 21, 2022, 11 pages.

International Patent Application No. PCT/US2021/060892, International Search Report and Written Opinion dated Mar. 21, 2022, 10 pages.

International Patent Application No. PCT/US2021/060893, International Search Report and Written Opinion dated Mar. 21, 2022, 9 pages.

International Patent Application No. PCT/US2021/060894, International Search Report and Written Opinion dated Mar. 21, 2022, 9 pages.

International Patent Application No. PCT/US2021/060895, International Search Report and Written Opinion dated Mar. 21, 9 pages.

International Patent Application No. PCT/US2021/060896, International Search Report and Written Opinion dated Mar. 14, 2022, 11 pages.

Juan Rendon et al. Structural combination of neural network models. 2016 IEEE 16th International Conference on Data Mining Workshops (ICDMW). IEEE Dec. 12, 2016, pp. 406-413. Section II; and figure 2.

Massimo Bonavita et al. Machine Learning for Model Error Inference and Correction. Journal of Advances in Modeling Earth Systems. Nov. 13, 2020, pp. 1-22. Section 2.1; and figure 1.

Md Manjurul Ahsan et al. Deep MLP-CNN Model Using Mixed-Data to Distinguish between COVID-19 and Non-COVID-19 Patients. Symmetry 2020. Sep. 16, 2020, pp. 1-14. Section 2; and figure 3.

U.S. Appl. No. 17/107,708, Office Action dated May 9, 2022, 57 pages.

U.S. Appl. No. 17/107,785, Final Office Action dated May 11, 2022, 9 pages.

U.S. Appl. No. 17/107,785, Office Action dated Mar. 29, 2022, 30 pages.

U .S. U.S. Appl. No. 17/107,824, Notice of Allowance dated May 2, 2022, 34 pages.

Van Hiep Phung et al. A High-Accuracy Model Average Ensemble of Convolutional Neural Networks for Classification of Cloud Image Patches on Small Datasets. Applied Sciences 2019. Oct. 23, 2019, pp. 1-16. Section 2; and figure 3.

Xueheng Qiu et al. Ensemble Deep Learning for Regression and Time Series Forecasting. 2014 IEEE Symposium on Computational Intelligence in Ensemble Learning (CIEL). IEEE, Dec. 9, 2014, pp. 1-6.

U.S. Appl. No. 17/107,824, Office Action dated Dec. 29, 2021, 30 pages.

(56) References Cited

OTHER PUBLICATIONS

U.S. Appl. No. 17/107,877, Final Office Action dated Dec. 29, 2021, 40 pages.
U.S. Appl. No. 17/107,785, Office Action dated Jul. 7, 2022, 21 pages.
U.S. Appl. No. 17/107,824, Notice of Allowance dated Jun. 7, 2022, 33 pages.
U.S. Appl. No. 17/107,830, Office Action dated Jun. 7, 2022, 51 pages.
U.S. Appl. No. 17/107,708, Final Office Action dated Aug. 19, 2022, 52 pages.
U.S. Appl. No. 17/107,714. Office Action dated Aug. 18, 2022, 66 pages.
U.S. Appl. No. 17/107,877, Notice of Allowance dated Aug. 22, 2022, 40 pages.

\* cited by examiner

SAFETY DETECTION CONTROLLER

BACKGROUND

In an effort to protect the safety of law enforcement officers, law enforcement agencies typically keep track of officers attending a dispatch. Tracking may occur via officer vehicles and/or officer personal devices. Each dispatch brings measurable safety concerns that law enforcement agencies can attempt to mitigate through dispatch policy. Dispatch policy may mandate particular safety measures for officers attending a dispatch event, based on the nature of the dispatch event and the nature of the individuals knowingly associated with the dispatch event. The safety measures are intended to protect the safety of the attending officers and the public at large and may include dispatching a predetermined number of attending officers, the use of body protective equipment, or a combination of both.

However, safety concerns determined by agency policy are based on information known prior to officers attending the dispatch event. On occasion, the safety of an attending officer may be impacted by events that are not commonly tied to the nature of the dispatch, and thus difficult to anticipate. Examples include the presence of individuals with communicable diseases, or the presence of individuals unknown to the attending officers with known/suspected affiliations to unlawful activities.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Figure 1:
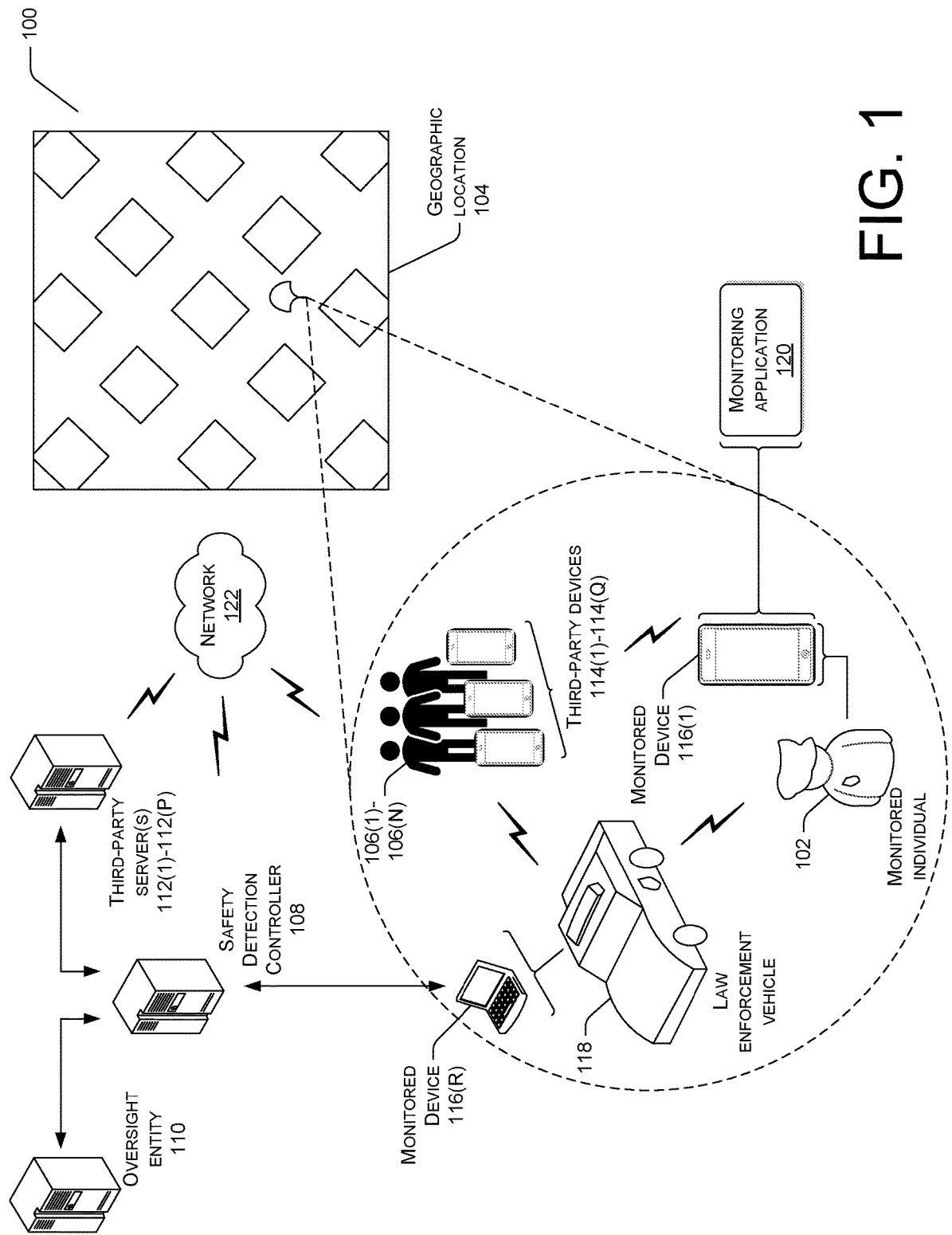
FIG. 1 illustrates a computing environment that facilitates the operation of the safety detection controller.

This disclosure describes techniques used to infer a likelihood that a safety concern may impact the health and safety of a monitored individual attending an event. Safety concerns may relate to occurrences that are not readily apparent to the monitored individual. In other words, the monitored individual may be unaware of the imminent safety concern. In the context of law enforcement, a law enforcement officer may attend a dispatch event that involves individuals with communicable diseases, or individuals with affiliations to unlawful activities. While an attending officer may appropriately prepare for anticipated safety concerns, they may be left exposed when facing unanticipated safety concerns.

Accordingly, this disclosure describes a safety detection controller that is configured to infer the likelihood of an unanticipated safety concern impacting a monitored individual. Sensor data may be captured from a monitored device of the monitored individual and analyzed to infer the identities of third-party individuals proximate to the monitored individual. In doing so, the safety detection controller may determine whether those identities pose a safety concern.

The safety detection controller may interact with a monitoring application that resides on a monitored device. The monitoring application may capture sensor data, such as audio data and video data proximate to the monitored individual. Sensor data may also include a geolocation of the monitored device as well as electronic handshake signal data tied to other third-party devices that wirelessly interact with the monitored device. Electronic handshake signal data may be associated with a wireless communication protocol such as, but not limited to, BLUETOOTH®.

Sensor data may be captured from sensors that reside on a monitored device or sensors that are remotely located but accessible via the monitored device. Referring to the earlier law enforcement example, the monitored device of a law enforcement officer may capture sensor data from sensors that reside on the monitored device and sensors that reside on a nearby law enforcement vehicle. The sensor data, in aggregate, may be relayed via the monitored device to the safety detection controller.

The safety detection controller may analyze the sensor data to identify third-party individuals proximate to the monitored individual. In a first example, the safety detection controller may analyze video data that captures images of third-party individuals and use one or more machine-learning algorithms to analyze visual biometric characteristics such as facial features or other distinctive body features (i.e. scars, tattoos, and/or forth). In doing so, the safety detection controller may compare those biometric features with registered visual biometric profiles to infer an identity of a third-party individual. The registered visual biometric profiles may reside on the safety detection controller, or alternatively, may reside remotely on a third-party server that is accessible by the safety detection controller.

In a second example, the safety detection controller may analyze audio data that captures a third-party individual's voice proximate to the monitored individual. Here, the safety detection controller may employ one or more machine-learning algorithms to analyze vocal biometric characteristics of the third-party individual's voice. Vocal characteristics may include an accent, tonality, refraction of sound, a frequency of a voice, a pitch of a voice, or any combination thereof. The analysis may involve a comparison of the vocal biometric features with registered vocal biometric profiles. The registered vocal biometric profiles may reside on the safety detection controller, or alternatively, may reside on a third-party server accessible by the safety detection controller.

In a third example, the safety detection controller may capture electronic handshake signal data from third-party devices proximate to the monitored device. The electronic handshake signal data may include a device identifier, such as a phone number, an International Mobile Subscriber Identity (IMSI) number, a Mobile Station International Subscriber Directory Number (MSISDN), or an International Mobile Equipment Identity (IMEI) number. The safety detection controller may use the device identifier to interact with a third-party server to identify the third-party device, and by extension, the third-party individual. The third-party server may correspond to a wireless carrier network, a core network server associated with a wireless carrier, and/or so forth.

In response to inferring an identity of third-party individuals proximate to a monitored device, the safety detection controller may determine whether those third-party individuals pose a safety concern. As an example, a safety concern may relate to the transmission of a communicable disease or the presence of a third-party individual with known/suspected affiliations to unlawful activities. In response to identifying a third-party individual, the safety detection controller may interact with third-party servers to determine whether the third-party individual poses a safety concern. For example, a third-party server may provide a medical database that records the identities of individuals known to be infected by a communicable disease. Alternatively, a third-party server may provide a criminal database that records the identities of individuals with known/suspected affiliations with unlawful activities.

In other examples, the safety detection controller may infer a safety concern based on an aggregate of sensor data received from multiple, monitored devices, rather than a single, monitored device associated with a single, monitored individual. For example, consider a concertgoer attending a live music event. At first, sensor data may be captured from the monitored device (i.e. via a monitoring application) associated with the concertgoer. In turn, the safety detection controller may analyze the sensor data to determine whether other monitored devices—associated with other concertgoers—are proximate to the concertgoer. If so, an aggregate of sensor data across the multiple monitored devices may be established, thereby better informing a safety concern for the concertgoer.

By using sensor data from other monitored devices, the safety detection controller may identify third parties that are further away from the concertgoer relative to those identified via the concertgoer's device. While the likelihood of a safety concern (i.e. safety score) may diminish with an increase in distance from the concertgoer, the benefit of reporting a diminished safety concern is preferred over a lack of messaging a safety concern, altogether.

Additionally, the safety detection controller may be configured to analyze the identities of third-party individuals in combination with other real-time data to determine whether a safety concern is likely to impact a monitored individual. Consider an example of a law enforcement officer attending a dispatch event. Here, the safety detection controller may interact with a network operations center (NOC) to capture event data relating to the dispatch event. The event data may include a geolocation of the dispatch event, nature of the dispatch event (i.e. traffic accident, residential or commercial disturbance, and/or so forth), the identities of third-parties likely to be present at the dispatch event, or any combination thereof.

Further, the safety detection controller may analyze the event data to determine an environmental context associated with the event. The environmental context is intended to account for environmental factors that may influence an inferred safety concern. For example, the environmental context may indicate whether a dispatch event occurs indoors or outdoors. If indoors, the inferred safety concern relating to a communicable disease may be elevated since the risk of acquiring a communicable disease indoors is more likely than outdoors. In another example, the environmental context may relate to ingress and egress points at the location of a dispatch event. If a dispatch event occurs in an environment with limited ingress and egress points, the inferred safety concern relating to third parties with known unlawful affiliations may be elevated.

Moreover, the safety detection controller may be configured to detect a safety concern based on an individual's own biometric data. In some examples, a monitored device may be equipped with sensors that capture biometric data associated with the monitored individual. Biometric data may include heart rate, body temperature, blood pressure, frequency of heart pulse waves, and/or so forth. Here, the biometric data may be analyzed to determine whether it is suggestive of an adverse health condition. In one example, the safety detection controller may compare captured biometric data with a registered biometric profile associated with the monitored individual. In turn, the safety detection controller may determine whether the biometric data is typical or atypical of the individual's nominal health profile. For example, a monitored individual may have a chronic underlying health condition, such as heart arrhythmia, that may impact their long-term health care but may not impact their imminent health and safety. As an underlying condition, the heart arrhythmia may be reflected on the monitored individual's registered biometric profile.

Subsequently, the safety detection controller may detect the heart arrhythmia based on captured biometric data (i.e. sensor data) via a monitored device. However, analysis of the biometric data, followed by a comparison with the individual's registered biometric profile, may infer that the biometric data is suggestive of the chronic underlying health condition, but not necessarily suggestive of an imminent adverse health condition.

Additionally, or alternatively, the safety detection controller may compare the biometric data with a registered biometric profile of a communicable disease. Here, registered biometric profiles of communicable diseases may highlight detectable symptoms that are indicative of a communicable disease. For example, an elevated body temperature while at rest may be symptomatic of influenza, a common communicable disease.

In some examples, the safety detection controller may interact with a third-party server to retrieve registered biometric profiles of communicable diseases. Registered biometric profiles may be retrieved based on communicable diseases that are temporally prevalent, geographically prevalent, or a combination of both. Geographic prevalence may be based on the geolocation of the monitored individual.

In various examples, the safety detection controller may generate a safety score based on the likelihood of a safety concern. Using the safety score as an indicator, alert messages may be sent to a monitored device warning of a possible safety concern. The content of each alert message may vary based on the magnitude of the safety score. A safety concern that is assigned a medium safety score may prompt the delivery of an alert message to a monitored device of the monitored individual. Alternatively, a safety concern that is assigned a high safety score may prompt the delivery of an alert message to the respective devices of a monitored individual and an oversight entity. The oversight entity may be a NOC that is responsible for dispatch events of a law enforcement officer, an office administrator responsible for the health and safety of employees (i.e. monitored individuals), or a parent/guardian responsible for the health and wellbeing of their child (i.e. monitored individual).

In one example, the safety detection controller may assign a high safety score to a safety concern associated with a law enforcement officer attending a dispatch event. Here, the safety detection controller may transmit an alert message to the attending officer's device (i.e. monitored device) and the NOC (i.e. oversight entity) that is responsible for the dispatch event. In this way, the alert message may inform the attending officer in real-time of the potential safety concern, while also providing the NOC with an opportunity to provide additional support to the attending officer. Support may be in the form of medical assistance when dealing with a communicable disease or making additional law enforcement officers available to deal with third party individuals with known unlawful affiliations.

While the techniques described within this disclosure focus on use-cases such as a concertgoer attending a live music event or a law enforcement officers attending a dispatch event, one of ordinary skill in the art may appreciate that variations and modifications can be made such that the safety detection controller may infer the likelihood of safety concerns of an individual attending any public or private event. For example, a school student or office employee may receive an alert message that other school students or work colleagues, nearby, may be infected with a communicable disease or hold affiliations with unlawful activities. As a result, an alert message indicating a safety concern may provide the school student or office employee with sufficient forewarning to implement appropriate safety measures.

Further, the term "techniques," as used herein, may refer to system(s), method(s), computer-readable instruction(s), module(s), algorithms, hardware logic, and/or operation(s) as permitted by the context described above and through the document.

FIG. 1 illustrates a computing environment that facilitates the operation of the safety detection controller. In the illustrated example, the computing environment 100 focuses on a law enforcement setting, whereby a law enforcement officer, as the monitored individual 102, is dispatched to a geographic location 104. At the geographic location 104, the law enforcement officer (i.e. monitored individual 102) may interact with the third-party individual(s) 106(1)-106(N) during their engagement at the dispatch event. In doing so, a monitored device associated with the law enforcement officer may relay sensor data to the safety detection controller 108 for analysis, which in turn, may relay an alert message of unanticipated safety concerns that may impact their health and safety.

In this example, the safety detection controller 108 may be communicatively coupled to an oversight entity 110. In the context of law enforcement activity, the oversight entity 110 may be a NOC. The NOC may be a command center that is part of a law enforcement agency, or a facility that is operated by a third-party that is providing services to a law enforcement agency. The NOC may be responsible for dispatch events for law enforcement officers and may owe a duty of care to a law enforcement officer (i.e. monitored individual 102). In this example, the safety detection controller 108 may receive event data relating to dispatch events from the NOC, and in turn, use the event data to infer whether a safety concern impacts a law enforcement officer. In turn, the safety detection controller 108 may relay an alert message to the NOC based on safety concerns impacting their law enforcement officer.

Further, the safety detection controller 108 may be communicatively coupled to one or more third-party server(s) 112(1)-112(P) to determine whether a safety concern impacts a monitored individual 102. The third-party server(s) 112(1)-112(P) may be used to identify the third-party individual(s) 106(1)-106(N) that interact with a monitored individual 102. In one example, third-party server(s) 112(1)-112(P) may correspond to a public and/or private identity databases accessible to the safety detection controller 108.

Third-party server(s) 112(1)-112(P) may also include telecommunications service providers that can identify the third-party individual(s) 106(1)-106(N) based on device identifiers of corresponding, third-party device(s) 114(1)-114(Q). In some examples, a monitoring application 120 that resides on the monitored device(s) 116(1)-116(R) may capture electronic handshake signal data from interacting third-party device(s) 114(1)-114(Q) associated with the third-party individual(s) 106(1)-106(N). The electronic handshake signal data may include device identifiers that a telecommunications service provider may use to identify the third-party device(s) 114(1)-114(Q), and by extension, the third-party individual(s) 106(1)-106(N).

Moreover, third-party server(s) 112(1)-112(P) may be used to infer a safety concern associated with a third-party individual. In some examples, the third-party server(s) 112(1)-112(P) may correspond to a criminal database of third-party individuals with known/suspected affiliations with unlawful activity. In other examples, the third-party server(s) 112(1)-112(P) may correspond to a medical database that records the identities of individuals known to be infected with a communicable disease. Third-party server(s) 112(1)-112(P) may also provide health profile data of a monitored individual. The health profile data may be used to determine whether biometric data associated with a monitored individual is indicative of an imminent safety concern, a managed chronic underlying health condition, or both.

In yet another example, third-party server(s) 112(1)-112(P) may include public servers that provide event data associated with a monitored individual. Event data may include dispatch event data for law enforcement activities, or public event data for public events, such as live concerts. Third-party server(s) 112(1)-112(P) may also include private servers that provide calendar data and profile data associated with a monitored individual 102.

Moreover, the safety detection controller 108 may be communicatively coupled to one or more monitored device(s) 116(1)-116(R). The monitored device(s) 116(1)-116(R) are associated with monitored individuals and may include electronic devices carried on the monitored individual's person, or proximate to the monitored individual, such as within a vehicle. In the illustrated example, the monitored individual 102, a law enforcement officer, may carry a monitored device on their person, and another monitored device may reside within their law enforcement vehicle 118.

Each of the monitored device(s) 116(1)-116(R) may include a monitoring application 120 that is configured to communicate with the safety detection controller 108. The monitoring application 120 may reside on the monitored device(S) 116(1)-116(R) or may reside on a remote server that is accessible by the monitored device(s) 116(1)-116(R). The monitoring application 120 may be configured to capture sensor data from the monitored device(s) 116(1)-116(R) and relay the sensor data to the safety detection controller 108 for analysis. The sensor data may include biometric data associated with the monitored individual 102, environmental sensor data (i.e. audio and video data) proximate to the monitored device(s) 116(1)-116(R), electronic handshake signal data associated with the third-party device(s) 114(1)-114(Q) proximate to a monitored device, or any combination thereof.

The monitored device(s) 116(1)-116(R) may relay sensor data to the safety detection controller 108 via the one or more network(s) 122. In turn, the safety detection controller 108 may analyze environmental sensor data and electronic handshake signal data to infer the identities of third-party individuals. The safety detection controller 108 may further analyze biometric data along with the environmental data to determine whether the monitored individual 102 is subject to an imminent safety concern.

In response to inferring a safety concern, the safety detection controller 108 may generate and deliver an alert message to the monitored device(s) 116(1)-116(R) based on an inferred safety concern. In some examples, an alert message is delivered to the monitored device(s) 116(1)-116(R) and an oversight entity 110. The oversight entity 110 may correspond to an entity that owes a duty of care to the monitored individual 102. In the illustrated example, the oversight entity 110 may correspond to the NOC. In other examples, the oversight entity 110 may correspond to an office administrator responsible for the health and safety of employees (i.e. monitored individuals), or a parent/guardian responsible for the health and wellbeing of their child (i.e. monitored individual).

The safety detection controller 108 may operate on one or more distributed computing resource(s). The one or more distributed computing resource(s) may include one or more computing device(s) that operate in a cluster or other configuration to share resources, balance load, increase performance, provide fail-over support or redundancy, or for other purposes. The one or more computing device(s) may include one or more interfaces to enable communications with other networked devices, such as the monitored device(s) 116(1)-116(R) via one or more network(s) 122.

The one or more network(s) 122 may include public networks such as the Internet, private networks such as an institutional and/or personal intranet, or some combination of a private and public network(s). The one or more network(s) can also include any type of wired and/or wireless network, including but not limited to local area network (LANs), wide area network(s) (WANs), satellite networks, cable networks, Wi-Fi networks, Wi-Max networks, mobile communications networks (i.e. 5G-NR, LTE, 3G, 2G), or any combination thereof.

Moreover, the monitored device(s) 116(1)-116(R) and the third-party device(s) 114(1)-114(Q) may include any sort of electronic device, such as a television unit, a multimedia streaming device, a cellular phone, a smartphone, a tablet computer, an electronic reader, a media player, a gaming device, a personal computer (PC), a laptop computer, etc. The monitored device(s) 116(1)-116(R) and the third-party device(s) 114(1)-114(Q) may also include network devices that act as intermediaries with the Internet. It is noteworthy that the Internet is accessible via one or more network(s) 122. In some examples, the monitored device(s) 116(1)-116(R) and the third-party device(s) 114(1)-114(Q) may include a subscriber identity module (SIM), such as an eSIM, to identify each device to a telecommunication service provider (also referred to herein, as "telecommunications network").

Figure 2:
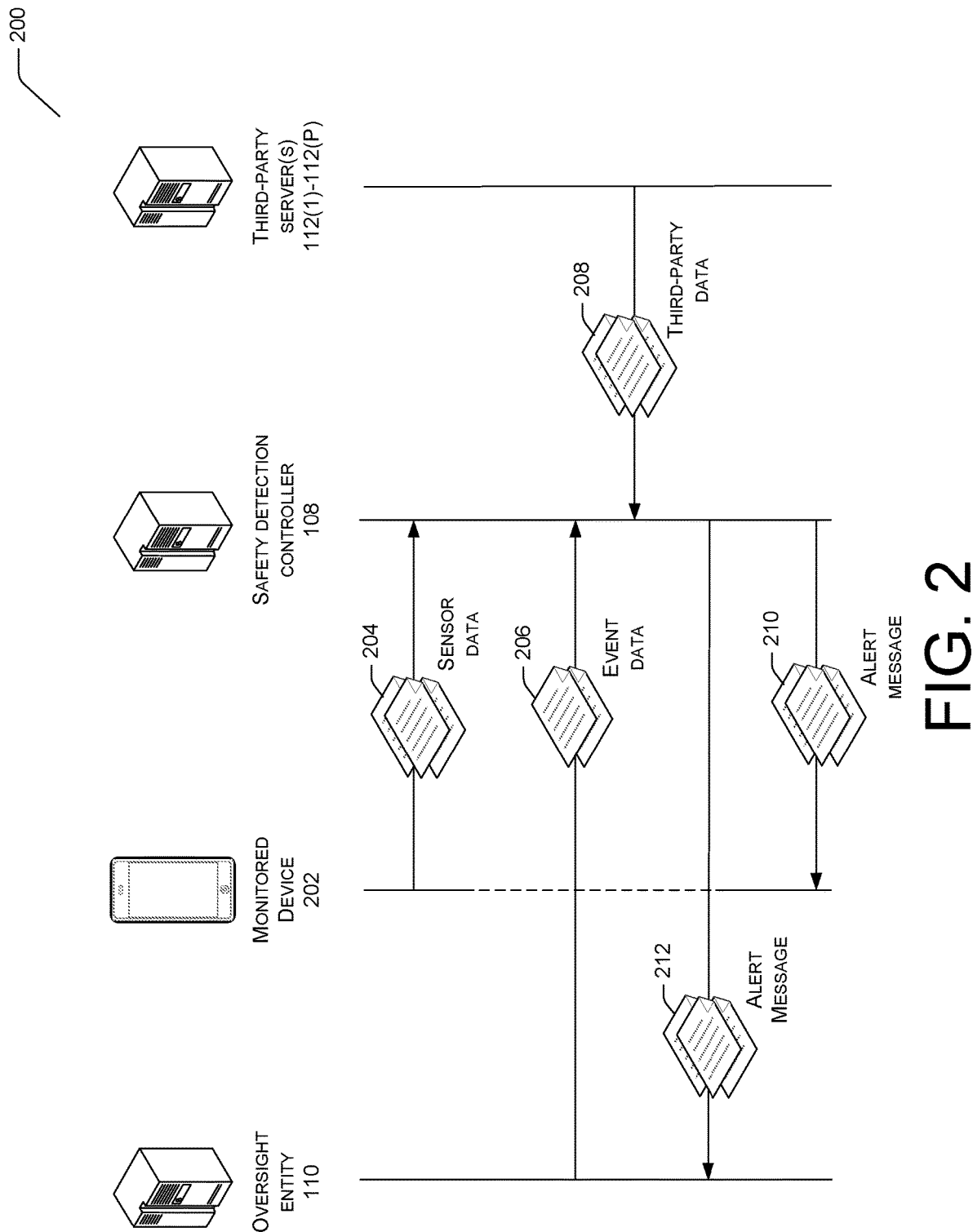
FIG. 2 illustrates a block diagram of a safety detection controller capturing and analyzing sensor data from a monitored device and further relaying an alert message based on an inferred safety concern.

FIG. 2 illustrates a block diagram of a safety detection controller 108 capturing and analyzing sensor data from a monitored device and further relaying an alert message based on an inferred safety concern. In the illustrated example, the monitored device 202 may capture sensor data 204 at a geographic location 104 associated with the monitored individual. The monitored device 202 may correspond to one of the monitored device(s) 116(1)-116(R). Sensor data 204 may include biometric data, environmental data, electronic handshake signal data, or any combination thereof.

The monitored device 202, via a monitoring application 120, may transmit the sensor data 204 to the safety detection controller 108. The safety detection controller 108 may analyze the sensor data 204 to infer the identities of third-party individuals proximate to the monitored individual 102 and further determine whether a safety concern impacts a monitored individual 102. Analysis of the safety concern may be based on the identities of the third-party individuals or the biometric data (i.e. sensor data 204).

In some examples, the safety detection controller 108 may interact with an oversight entity 110, such as a NOC to request event data 206. In the context of law enforcement activity, the event data 206 may help determine the nature of a dispatch event. Event data 206 may also instructive in determining the environmental context of the dispatch event. For example, the event data may be used to determine known ingress and egress points at a dispatch event location.

Also, the safety detection controller 108 may capture third-party data 208 from one or more third-party server(s) 112(1)-112(P). The third-party data 208 may be used to identify third-party individuals proximate to a monitored individual and further determine whether a safety concern may impact a monitored individual. Without limitation, third-party server(s) 112(1)-112(P) may include a telecommunication service provider server for identifying third-party individuals based on device identifiers, a criminal database for identifying third-party individuals with known/suspected affiliations with unlawful activity, a medical database for identifying third-party individuals known to be infected with a communicable disease, public services for providing event data associated with a monitored individual, private servers for providing calendar data and profile data associated with a monitored individual, or any combination thereof.

Further, the safety detection controller 108 may analyze the sensor data 204 to determine whether a safety concern impacts a monitored individual. Event data 206 and third-party data 208 captured from an oversight entity 110 and third-party server(s) 112(1)-112(P) may help instruct the analysis. In response to determining that a safety concern may impact a monitored individual, the safety detection controller 108 may generate an alert message 210 for delivery to the monitored individual. The alert message 210 may identify the safety concern and its likelihood of impacting the monitored individual. The likelihood of impact may be expressed as a safety score. In some examples, an additional alert message 212 may be sent to an oversight entity 110 that owes a duty of care to the monitored individual. The oversight entity 110 may be a NOC, an employer, an event organizer/administrator, or a parent/guardian.

Figure 3:
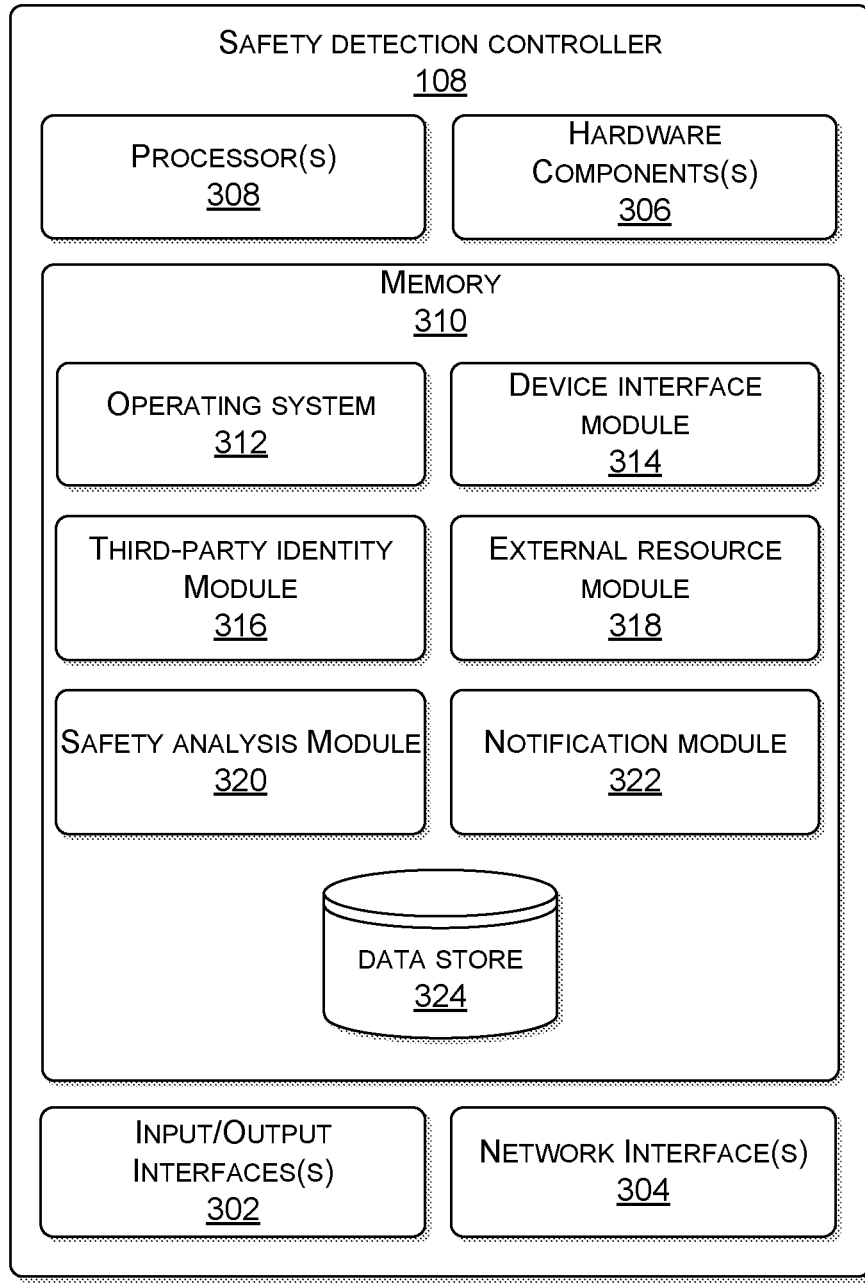
FIG. 3 illustrates various components of a safety detection controller.

FIG. 3 illustrates various components of a safety detection controller. The safety detection controller may interact with monitored devices to determine whether monitored individuals may be subject to imminent and unanticipated safety concerns that may impact their health, safety, and wellbeing. Safety concerns may involve their exposure to third-party individuals with communicable diseases or individuals with affiliations to unlawful activities. If a safety concern is identified, the safety detection controller 108 may generate alert messages for delivery to the monitored individuals, to highlight the imminent safety concern.

The safety detection controller 108 may include input/output interface(s) 302. The input/output interface(s) 302 may include any type of output interface known in the art, such as a display (e.g. a liquid crystal display), speakers, a vibrating mechanism, or a tactile feedback mechanism. Input/output interface(s) 302 also include ports for one or more peripheral devices, such as headphones, peripheral speakers, or a peripheral display. Further, the input/output interface(s) 302 may further include a camera, a microphone, a keyboard/keypad, or a touch-sensitive display. A keyboard/keypad may be a push-button numerical dialing pad (such as on a typical telecommunication device), a multi-key keyboard (such as a conventional QWERTY keyboard), or one or more other types of keys or buttons, and may also include a joystick-like controller and/or designated navigation buttons, or the like.

Additionally, the safety detection controller 108 may include network interface(s) 304. The network interface(s) 304 may include any sort of transceiver known in the art. For example, the network interface(s) 304 may include a radio transceiver that performs the function of transmitting and receiving radio frequency communications via an antenna. Also, the network interface(s) 304 may include a wireless communication transceiver and a near-field antenna for communicating over unlicensed wireless Internet Protocol (IP) networks, such as local wireless data networks and personal area networks (e.g. Bluetooth or near field communication (NFC) networks). Further, the network interface(s) 304 may include wired communication components, such as an Ethernet port or a Universal Serial Bus (USB). Hardware component(s) 306 may include additional hardware interface, data communication hardware, and data storage hardware.

Further, the safety detection controller 108 may include one or more processor(s) 308 that are operably connected to memory 310. In at least one example, the one or more processor(s) 308 may be a central processing unit(s) (CPU), graphics processing unit(s) (GPU), or both a CPU and GPU or any other sort of processing unit(s). Each of the one or more processor(s) 308 may have numerous arithmetic logic units (ALUs) that perform arithmetic and logical operations as well as one or more control units (CUs) that extract instructions and stored content from processor cache memory, and then executes these instructions by calling on the ALUs, as necessary during program execution. The one or more processor(s) 308 may also be responsible for executing all computer applications stored in the memory, which can be associated with common types of volatile (RAM) and/or non-volatile (ROM) memory.

In some examples, memory 310 may include system memory, which may be volatile (such as RAM), non-volatile (such as ROM, flash memory, etc.), or some combination of the two. The memory may also include additional data storage devices (removable and/or non-removable) such as, for example, magnetic disks, optical disks, or tape.

The memory 310 may further include non-transitory computer-readable media, such as volatile and nonvolatile, removable and non-removable media implemented in any method or technology for storage of information, such as computer-readable instructions, data structures, program modules, or other data. System memory, removable storage, and non-removable storage are all examples of non-transitory computer-readable media. Examples of non-transitory computer-readable media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory medium which can be used to store the desired information.

In the illustrated example, the memory 310 may include an operating system 312, a device interface module 314, a third-party identity module 316, an external resource module 318, a safety analysis module 320, a notification module 322, and a data store 324. The operating system 312 may be any operating system capable of managing computer hardware and software resources. The operating system 312 may include an interface layer that enables applications to interface with the input/output interface(s) 302 and the network interface(s) 304.

The device interface module 314 may be configured to capture sensor data from monitoring applications associated with monitored devices. The sensor data is intended to capture environmental data proximate to each monitored device. Further, the device interface module 314 may transmit alert messages to the monitored devices in response to a determination that a safety concern exists. Alert messages may also be sent to oversight entities that are associated with monitored devices.

The device interface module 314 may poll monitoring applications for sensor data continuously, per a predetermined schedule, or in response to a triggering event. The predetermined schedule may be based on any time interval, such as one hour, 30 minutes, 15 minutes, or 5 minutes. The triggering event may correspond to an indication that a real-time event is in progress, such as a dispatch event in the context of law enforcement activity or a live entertainment event in the context of a public activity.

In some examples, the device interface module 314 may be configured to poll multiple monitoring applications proximate to a [primary] monitored device. In doing so, sensor data, including geolocation data, from each of the monitoring applications are aggregated and analyzed to support an expansive understanding of safety concerns that may impact the [primary] monitored device.

The third-party identity module 316 may be configured to infer an identity of third-party individuals proximate to the monitored device. More specifically, the third-party identity module 316 may employ one or more machine-learning algorithms to analyze sensor data received from the device interface module 314 to infer an identity of third-party individuals proximate to the monitored device. The sensor data may include audio data, visual data, or electronic handshake signal data. The audio and visual data may be compared to registered biometric profiles to infer an identity of third-party individuals. In some examples, the similarity between the biometric data and the registered biometric profiles may be determined by measuring the Euclid distance between the current environmental metadata and datapoints of the analysis model. The registered biometric profiles may be accessible via the external resource module 318. The electronic handshake signal data may include device identifiers that may be used to identity third-party individuals. The association between device identifiers and third-party individuals may be established via a telecommunications service provider accessible via the external resource module 318.

Further, the one or more trained machine-learning algorithms may make use of techniques such as supervised learning, unsupervised learning, semi-supervised learning, naive Bayes, Bayesian network, decision trees, neural networks, fuzzy logic models, and/or probabilistic classification models.

The external resource module 318 may be configured to interact with third-party servers as part of inferring an identity of third-party individuals proximate to the monitored device and determining the likelihood of a safety concern. For identifying third-party individuals, the third-party server may correspond to a repository of audio or visual biometric data of third-party individuals. Also, the third-party server may be associated with a telecommunications service provider to identify third party individuals based on device identifiers. For determining whether a safety concern exists, the third-party server may be a medical database that records the identities of individuals known to be infected by a communicable disease, a criminal database that records the identities of individuals with known unlawful affiliations, and/or so forth.

The external resource module 318 may selectively access third-party servers based on the geolocation of the monitored individual. For example, publicly available event data (i.e. via a third-party server) may be used to determine whether the monitored individual is attending a public event, such as a concert. Also, the external resource module 318 may access calendar information associated with the monitored individual, which may be used to determine the nature of the event, based on geolocation data, the time of day, and the day of the week.

The safety analysis module 320 may be configured to determine the likelihood of a safety concern. The safety analysis module 320 may use one or more machine-learning algorithms to analyze inferred third-party identities to determine whether those identities pose a safety concern to the monitored individual. In one example, the safety analysis module 320 may interact with a third-party server, via the external resource module 318, to determine whether the third-party individuals are included on a list of individuals that have contracted a communicable disease (i.e. third-party medical database), or a list of individuals with known/suspected affiliations to unlawful activity (i.e. third-party criminal database).

The safety analysis module 320 may further determine an environmental context associated with the current geolocation of a monitored individual. By determining an environmental context, the safety analysis module 320 may account for environmental factors that influence a safety concern. In the context of law enforcement activities, the environmental context may relate to known ingress and egress points at a dispatch event location. In the context of law enforcement activity, the safety analysis module 320 may glean environmental context data from an oversight entity 110, such as a NOC (i.e. dispatch event data). In the context of public activity, the environmental context may be gleaned from a public or private third-party server.

Further, the safety analysis module 320 may analyze biometric data associated with the monitored individual to determine whether the biometric data is suggestive of an adverse health condition. The biometric data may be analyzed relative to a registered biometric profile associated with the monitored individual. The registered biometric profile may detail an individual's nominal health condition including indications of chronic underlying conditions. Therefore, the safety analysis module 320 may infer whether the biometric data is typical or atypical of the individual's nominal health profile. The individual's nominal health profile may be retrieved from the data store 324, or alternatively, from a third-party server via the external resource module 318. The third-party server may be a NOC (i.e. in a law enforcement context), or a public or private medical database server, and/or so forth.

Additionally, or alternatively, the biometric data may be analyzed relative to a registered template associated with a communicable disease. The safety analysis module 320 may identify communicable diseases for analysis based on temporal prevalence or geographic prevalence. Geographic prevalence may be based on the geolocation of the monitored individual.

In some examples, the safety analysis module 320 may generate a safety score based at least in part on the likelihood of a safety concern. The safety score may be alpha-numeric (i.e. 0 to 10, or A to F), descriptive, (i.e. low, medium, or high), based on color (i.e. green, yellow, red), or any other suitable rating scale. A high safety score (i.e. 7 to 10, high, red) may indicate a safety concern that is very likely to impact an individual. Examples include identifying a nearby third-party with a communicable disease or known major unlawful affiliations. A medium safety score (i.e. 4 to 6, medium, yellow) may indicate a safety concern that may impact an individual. Examples include identifying a third-party with a communicable disease or known unlawful affiliation that is present but not necessarily nearby. A low safety score (i.e. 1 to 3, low, green) may indicate an unlikely presence of a safety concern.

The notification module 322 may be configured to generate alert messages for delivery to a monitored device. The content of the alert messages may vary based on the inferred safety concern. For example, if a safety concern is inferred as very likely, the alert message may indicate the same in a clear and concise warning. In some examples, the notification module 322 may generate an alert message based at least in part on the magnitude of a safety score. An alert message may be generated only if the safety score is greater than or equal to a predetermined safety threshold set by an operator of the safety detection controller 108.

The notification module 322 may generate additional alert messages for delivery to an oversight entity 110, which may owe a duty of care to the monitored individual. The oversight entity 110 may be a NOC that is responsible for dispatch events of a law enforcement officer, an office administrator responsible for the health and safety of employees (i.e. monitored individuals), or a parent/guardian responsible for the health and wellbeing of their child (i.e. monitored individual).

The data store 324 may include a repository of registered biometric profiles (i.e. monitored individuals and communicable diseases), a profile of the monitored individual, and any other data pertinent to an operation of the safety detection controller 108.

Figure 4:
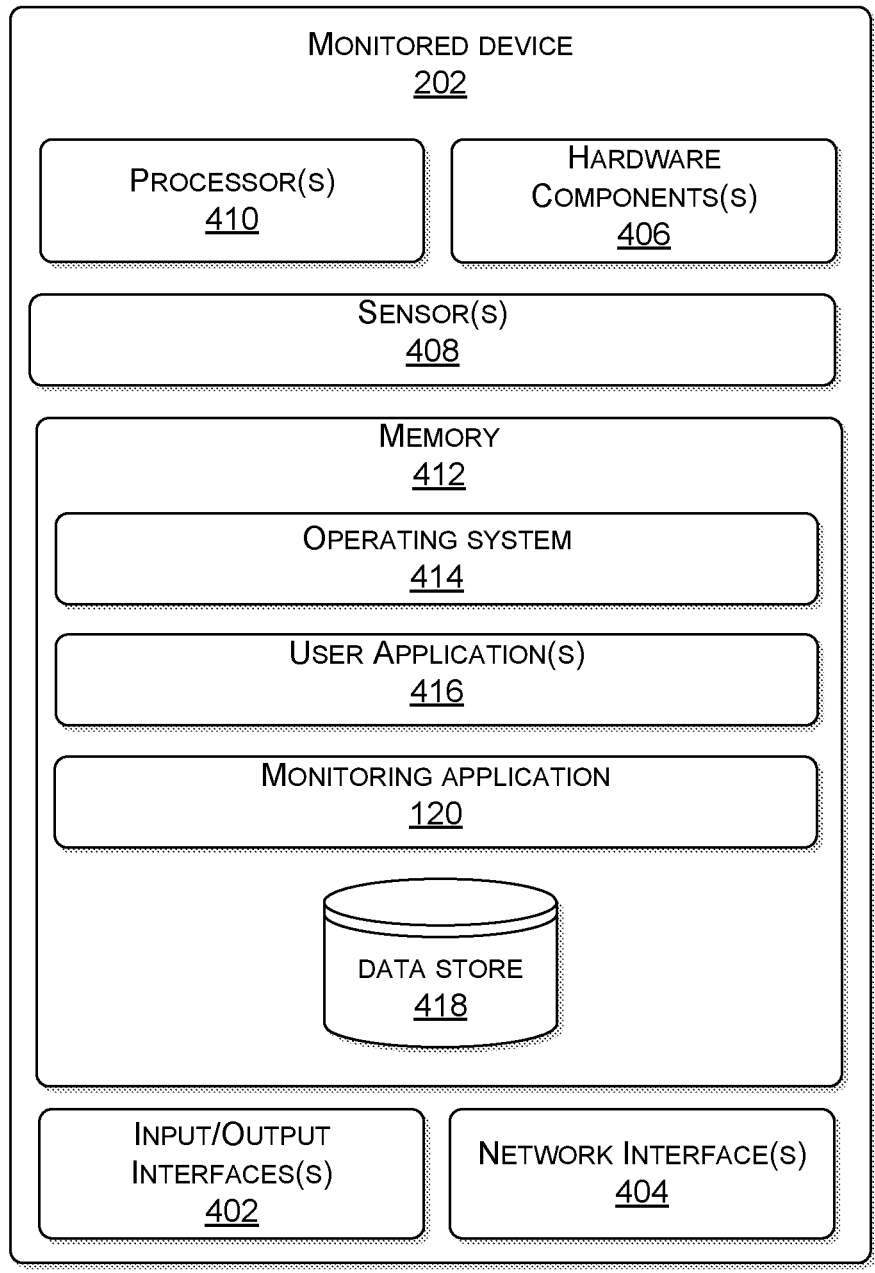
FIG. 4 illustrates various components of a monitored device that is communicatively coupled to a safety detection controller.

FIG. 4 illustrates various components of a monitored device that is communicatively coupled to a safety detection controller. In the illustrated example, the monitored device 202 may be configured to capture and relay sensor data to a safety detection controller 108 to determine whether a monitored individual 102 may be at risk of an unanticipated safety concern. In turn, the monitored device 202 may receive, from a safety detection controller, an alert message warning of the possible safety concern.

The monitored device 202 may include input/output interface(s) 402 and network interface(s) 404. The input/output interface(s) 402 may be similar to input/output interface(s) 302, and the network interface(s) 404 may be similar to network interface(s) 304. The monitored device 202 may include hardware component(s) 406. The hardware component(s) 406 may be similar to the hardware component(s) 306.

The monitored device 202 may include sensor(s) 408 that are configured to capture sensor data that reflect an environment proximate to the monitored device 202, and by extension, the monitored individual. Sensor(s) 408 may include a GPS sensor to determine a geolocation of the monitored device 202, a microphone to capture audio data, and a camera to capture image and video data. It is noteworthy that sensor data may also include electronic handshake signal data relating to other third-party devices proximate to the monitored device 202. Here, the electronic handshake signal data may be captured by the sensor(s) 408 or the network interface(s) 404.

Sensor(s) 408 may further include biometric sensors configured to capture biometric data associated with the monitored individual. Biometric sensors may include an optical heart sensor configured to detect pulse waves for variability in beat-to-beat intervals. Irregular beat-to-beat intervals may be suggestive of atrial fibrillation.

The monitored device 202 may include one or more processor(s) 410 that are operably connected to memory 412. The one or more processor(s) 410 may be similar to the one or more processor(s) 308, and the memory 412 may be similar to the memory 310.

The memory 412 may include an operating system 414, user application(s) 416, a monitoring application 120, and a data store 418. The operating system 414 may be any operating system capable of managing computer hardware and software resources. The operating system 414 may include an interface layer that enables applications to interface with the input/output interface(s) 402 and the network interface(s) 404.

User application(s) 416 may include any application executable via the monitored device 202. The user application(s) 416 may reside in the memory 412 of the monitored device 202 or reside on a separate server that is remotely accessible by the monitored device 202.

The monitoring application 120 may be configured to interact with the safety detection controller 108. In the illustrated example, the monitoring application 120 may reside on the monitored device. In another example, the monitoring application 120 may reside on a remote server that is accessible by the monitored device 202. In each case, the monitoring application 120 may capture and relay sensor data to the safety detection controller 108, and further present alert messages on a display of the monitored device 202. The monitoring application 120 may capture the sensor data continuously, per a predetermined schedule, or in response to a triggering event. The predetermined schedule may be based on any time interval, such as one hour, 30 minutes, 15 minutes, or 5 minutes. The triggering event may correspond to an elevated measurement of biometric data that exceeds a predetermined threshold. For example, a heart rate of about 120 beats per minute or a body temperature of 100 degrees Fahrenheit may correspond to a triggering event. Also, with regards to capturing sensor data of an environment proximate to the monitored device 202, a triggering event may be based on the geolocation of the monitored device 202 (i.e. aligning geolocation with a dispatch event or a calendar event), a change in geolocation, detecting audio or video signals, detecting a change in audio or video signals or detecting a poll request for electronic handshake signal data.

The data store 418 may include a repository of sensor data captured by the sensor(s) 408, electronic handshake signal data captured by the sensor(s) 408 or the network interface(s) 404, profile data of the monitored individual associated with the monitored device 202, and any other data pertinent to an operation of the monitored device 202. Profile data may also include calendar information associated with the monitored individual.

FIGS. 5 through 8 present processes 500 through 800 that relate to operations of the Safety detection controller 108. Each of the processes 500 through 800 illustrate a collection of blocks in a logical flow chart, which represents a sequence of operations that can be implemented in hardware, software, or a combination thereof. In the context of software, the blocks represent computer-executable instructions that, when executed by one or more processors, perform the recited operations. Generally, computer-executable instructions may include routines, programs, objects, components, data structures, and the like that perform particular functions or implement particular abstract data types. The order in which the operations are described is not intended to be construed as a limitation, and any number of the described blocks can be combined in any order and/or in parallel to implement the process. For discussion purposes, the processes 500 through 800 are described with reference to the computing environment 100 of FIG. 1.

Figure 5:
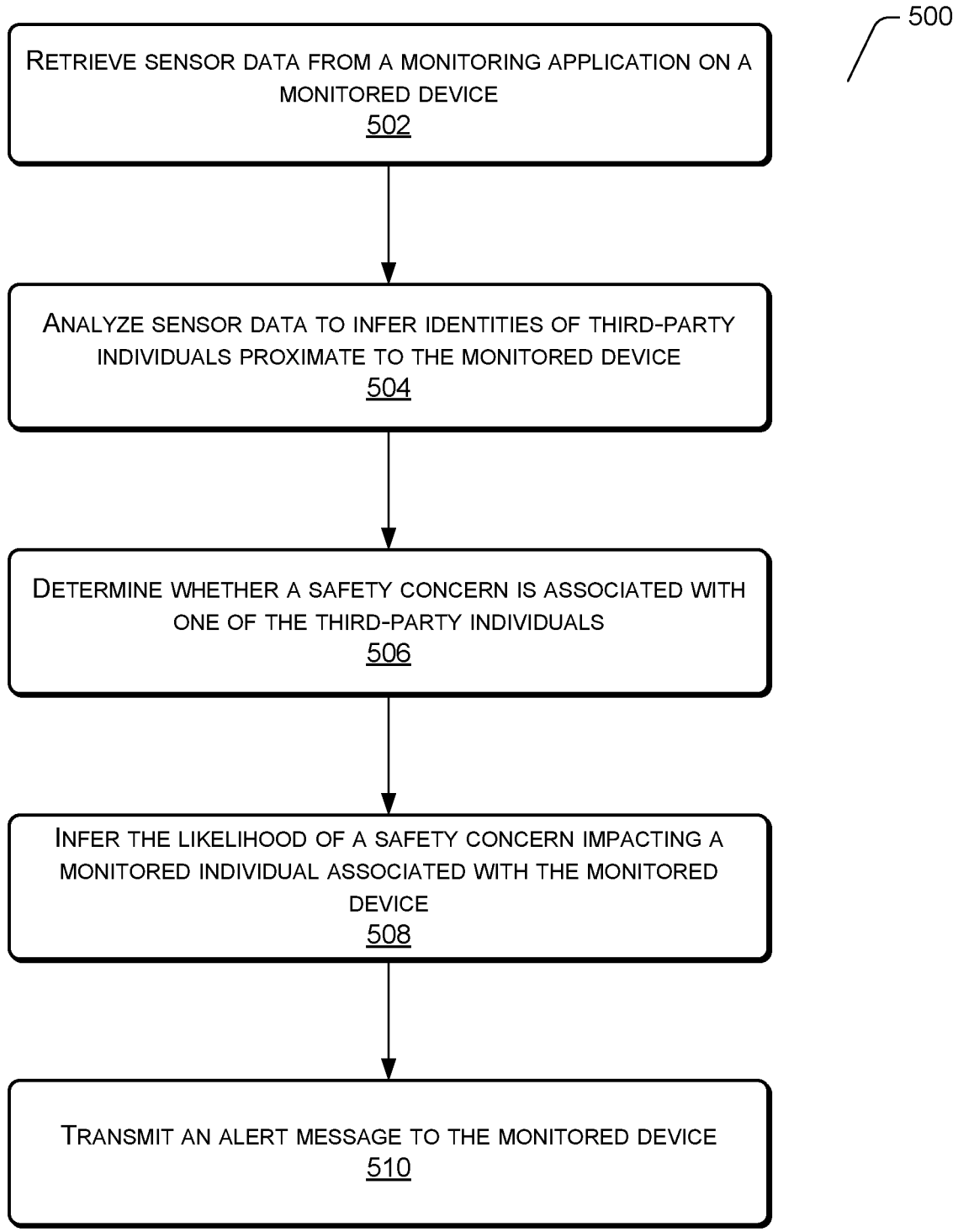
FIG. 5 illustrates a process for inferring the likelihood of a safety concern that impacts a monitored individual.

FIG. 5 illustrates a process for inferring the likelihood of a safety concern that impacts a monitored individual. The monitored individual may be a concert-attendee, a law enforcement officer, or any other person and presents themselves in a public place. Process 500 is described from the perspective of the safety detection controller, which is configured to determine a safety concern based on sensor data captured from a monitored device associated with the monitored individual.

At 502, the safety detection controller may receive sensor data from a monitoring application associated with the monitored device associated with the monitored individual. The monitoring application may reside on the monitored device or may be accessible via the monitored device. Further, the sensor data may include audio data, video data, geolocation data, electronic handshake signal data, or any combination thereof. Electronic handshake signal data may be tied to other third-party devices proximate to the monitored device and may be associated with a wireless communication protocol such as BLUETOOTH (Registered Trademark).

At 504, the safety detection controller may analyze the sensor data to infer the identities of third-party individuals proximate to the monitored device. By way of example, the safety detection controller may analyze vocal biometric features of a third-party individual's voice relative to registered vocal biometric profiles. An identity of a third-party may be inferred based on the similarity between the vocal biometric features and registered vocal biometric profile exceeding a predetermined similarity threshold. The similarity may be determined by measuring the Euclid distance between the vocal biometric features and the registered vocal biometric profile.

At 506, the safety detection controller may determine whether a safety concern is associated with the third-party individual identified in process step 504. In some examples, the safety detection controller may interact with a third-party server to determine whether the third-party individual poses a safety concern. The third-party server may include a criminal database of individuals with known/suspected affiliations to unlawful activities, a medical database that records individuals known to be infected with a communicable disease, or a combination of both. In each instance, the safety detection controller may determine whether the third-party individuals are listed on the medical or criminal databases.

At 508, the safety detection controller may infer the likelihood of a safety concern impacting the monitored individual associated with the monitored device. Here, a safety concern may be implied if the third-party individuals are listed on the medical or criminal databases. In some examples, the safety detection controller may determine a safety score based on the likelihood of the safety concern. The safety score may consider the proximity of third-party individuals to the monitored individual and the nature of the safety concern (i.e. communicable disease or affiliation with unlawful activity).

At 510, the safety detection controller may transmit an alert message to the monitored device associated with the monitored individual. The content of the alert message may vary based on the safety score. In some examples, an additional alert message may be transmitted to an oversight entity associated with the monitored individual. The oversight entities may owe a duty of care to the monitored individual or may be associated with the monitored individual based on a contractual agreement. In one example, the oversight entity may be a NOC that is responsible for dispatch events of a law enforcement officer (i.e. monitored individual). In other examples, the oversight entity may be a parent/guardian of the monitored individual, an office administrator responsible for the health and safety of employees (i.e. monitored individual), or a concert venue organizer responsible for the health and safety of concert-attendees (i.e. monitored individual). In any case, the additional alert message may be transmitted to the oversight entity based on the severity of the safety concern (i.e. magnitude of the safety score) relative to the monitored individual.

Figure 6:
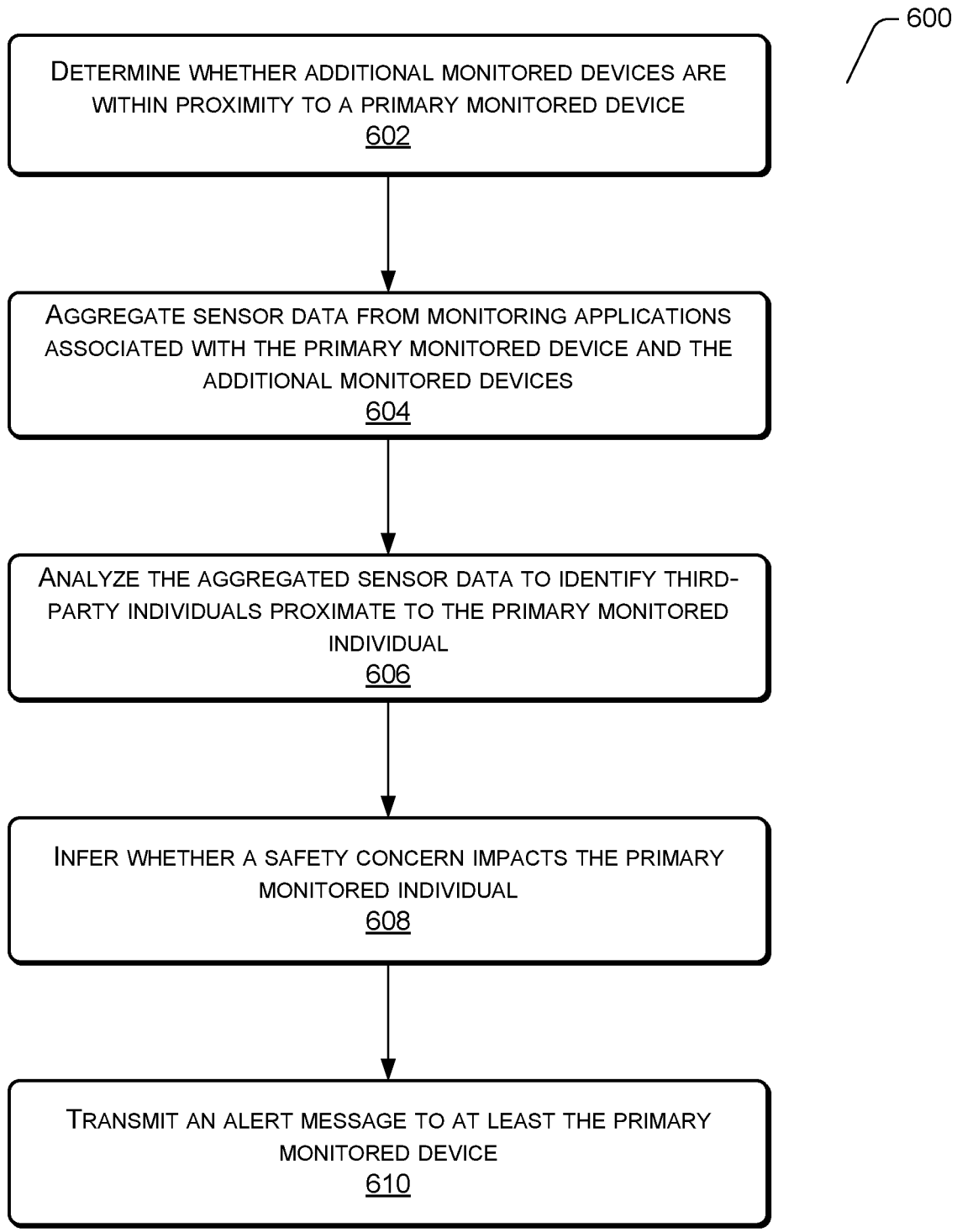
FIG. 6 illustrates a process for determining a safety concern of a primary monitored individual based on sensor data gleaned from a plurality of other monitored individuals within the same proximate geolocation.

FIG. 6 illustrates a process for determining a safety concern of a primary monitored individual based on sensor data gleaned from a plurality of other monitored individuals within the same proximate geolocation. Process 600 is described from the perspective of a safety detection controller that is establishing the safety concern of the primary monitored individual.

At 602, the safety detection controller may determine whether additional monitored devices are within proximity to a primary monitored device. Detecting the presence of monitored devices may be based on detecting the presence of monitoring applications on the monitored devices, themselves. The sensor data associated with each monitored device, received via their respective monitoring applications, may include geolocation data. Geolocation data may be used to determine the relative locations of each monitored device.

At 604, the safety detection controller may aggregate sensor data from monitoring applications associated with the primary monitored device and the additional monitored devices. The sensor data may include audio data, video data, electronic handshake signal data, geolocation data, or any combination thereof.

At 606, the safety detection controller may analyze the aggregated sensor data to identify third-party individuals (e.g. individuals that are not associated with a monitored device) that are proximate to the primary monitored individual. Since additional sensor data is being collected from additional monitored devices, the safety detection controller may identify third-party individuals that are further away from the primary monitored individual than what would have normally been determined using only the sensor data from the primary monitored device. In doing so, the primary monitored individual, who may be in possession of the primary monitored device, is provided with an alert of a third-party individual that may pose a safety concern.

At 608, the safety detection controller may infer whether a safety concern impacts the primary monitored individual. The safety concern may be reflected as a safety score. The safety score may be calculated based on the nature of the safety concern (i.e. third party with a communicable disease or a third party with an affiliation to unlawful activity) and a relative distance of the third-party individual to the primary monitored individual.

At 610, the safety detection controller may transmit an alert message to at least the primary monitored device based at least in part on the safety score being greater than or equal to a predetermined safety threshold. The predetermined safety threshold may be established by the primary monitored individual, an operator of the safety detection controller, or an independent controller with knowledge of the type of safety concern (i.e. third party with a communicable disease or a third party with an affiliation to unlawful activity). The independent controller may be a medical agency for safety concerns relating to communicable diseases, or a law enforcement agency for safety concerns relating to unlawful activity.

Figure 7:
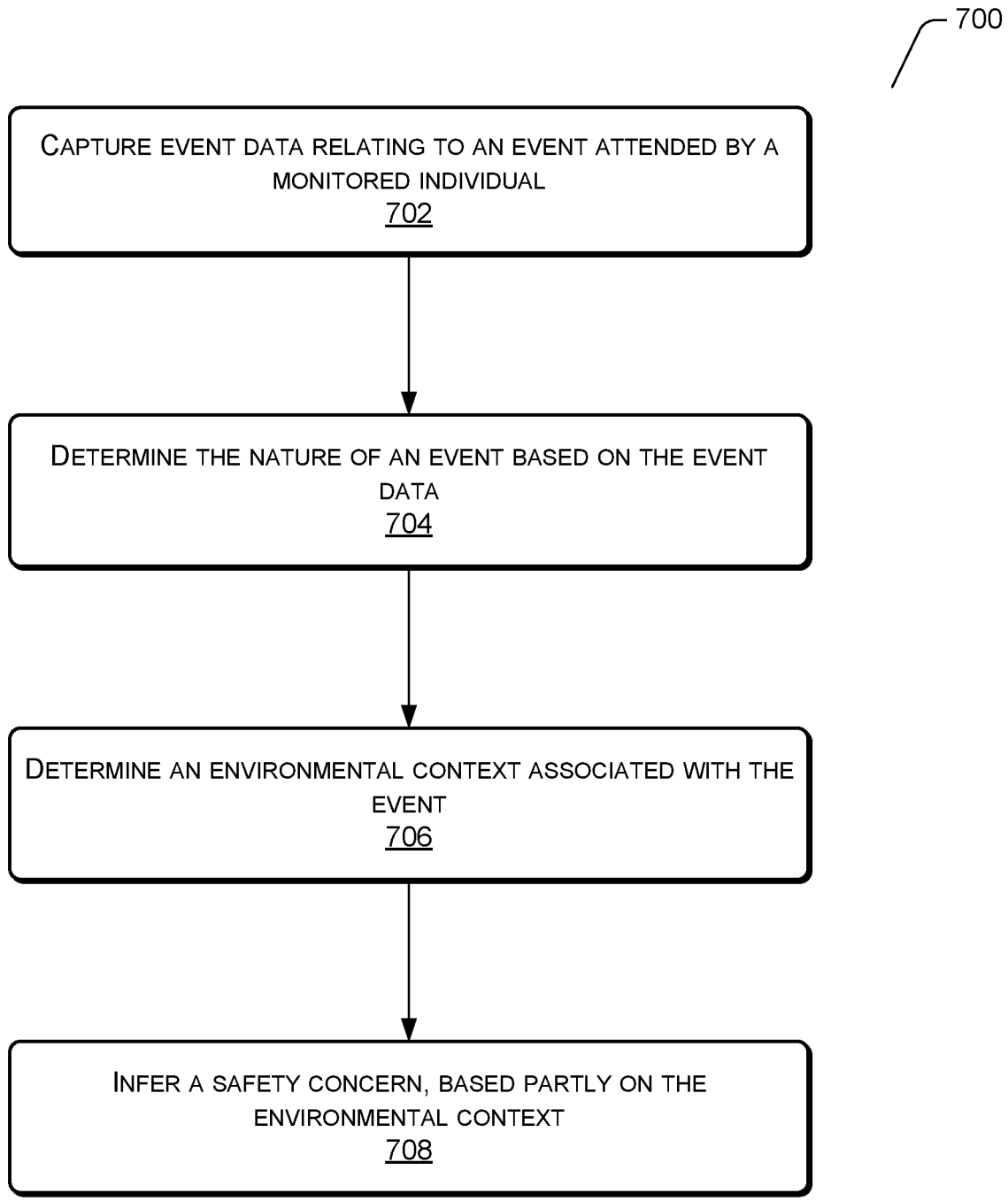
FIG. 7 illustrates a process for inferring a safety concern based on event data relating to an event attended by a monitored individual.

FIG. 7 illustrates a process for inferring a safety concern based on event data relating to an event attended by a monitored individual. In the context of determining a safety concern, an event may describe the purpose for which the monitored individual is present at a geolocation. In the context of law enforcement, the event may be a dispatch event, such as a domestic or residence disturbance, or a traffic incident. In the context of a concert-attendee, the event may be live entertainment. Process 700 further describes determining the environmental context associated with an event. Environmental context accounts for environmental factors that influence a safety concern. Process 700 is described from the perspective of the safety detection controller, which determines an environmental context, infers the identity of third-party individuals, and further determines a corresponding safety concern.

At 702, the safety detection controller may capture event data relating to an event attended by a monitored individual. Event data may be captured in several ways. In a law enforcement context, the safety detection controller may interact with a NOC to capture event data of a dispatch event. In a public environmental context, the safety detection controller may use geolocation data of monitored individuals to determine whether a public event is occurring at the geolocation attended by the monitored individual. Access to third party servers may inform the safety detection controller of real-time public events, based on geolocation data. Additionally, or alternatively, access to calendar data associated with the monitored individual, via their monitored device, may be used to capture event data.

At 704, the safety detection controller may determine the nature of an event based on the event data. In some examples, the safety detection controller may combine event data with sensor data to determine the nature of the event. For example, geolocation data (i.e. sensor data) and publicly available event data (i.e. via a third-party server) may be used to determine whether the monitored individual is attending a public event, such as a concert. Similarly, geolocation data (i.e. sensor data) and dispatch event data may be used to determine whether a law enforcement officer (i.e. monitored individual) is attending a dispatch event. In a third example, a combination of calendar data and at least one of geolocation data or publicly available event data may be used to determine the nature of an event.

At 706, the safety detection controller may determine an environmental context associated with the event. The environmental context is intended to account for environmental factors that influence a safety concern. When dealing with a communicable disease, the environmental context may relate to whether the event occurs indoors or outdoors. Similarly, when dealing with law enforcement activities, the environmental context may relate to ingress and egress points at a dispatch event location.

At 708, the safety detection controller may infer a safety concern, based partly on the environmental context. For example, the safety concern may be inferred for the monitored individual. While the safety detection controller may identify a safety concern based on the analysis of third-party individuals proximate to a monitored individual, the environmental context may be used to determine the degree of risk associated with the safety concern, and the degree of risk may be expressed as a safety score. For example, the risk of contracting a communicable disease may increase in an indoor environment relative to an outdoor environment. Similarly, the risk to the safety of a law enforcement officer attending a dispatch event may increase with limited ingress and egress points at the dispatch location.

Figure 8:
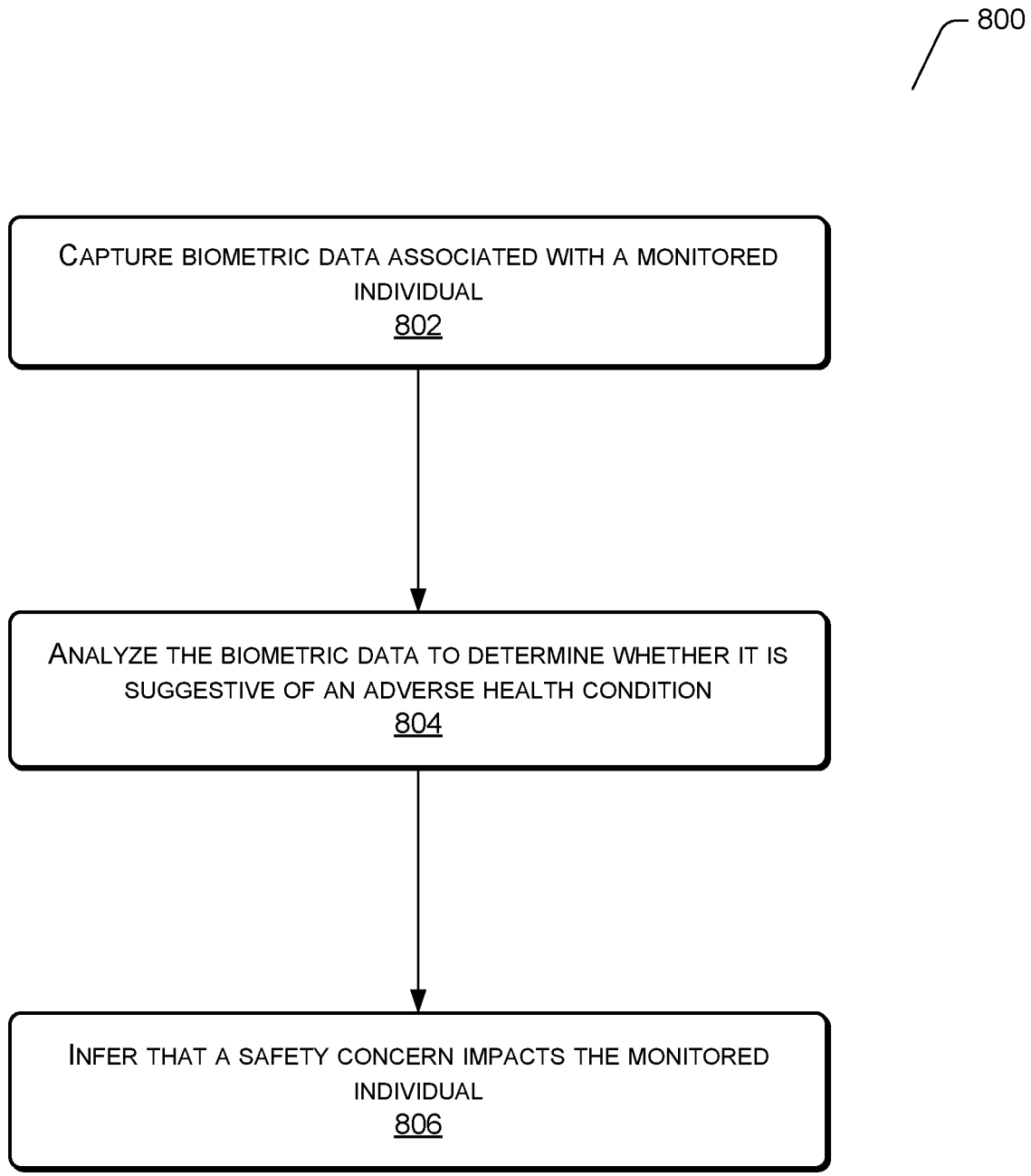
FIG. 8 illustrates a process for inferring a safety concern based on biometric data associated with a monitored individual.

FIG. 8 illustrates a process for inferring a safety concern based on biometric data associated with a monitored individual. The biometric data may be captured via a monitored device associated with the monitored individual and may be used to determine whether it is suggestive of an adverse health condition. Process 800 is described from the perspective of the safety detection controller, which receives biometric data from a monitored device, and further determines a corresponding safety concern.

At 802, the safety detection controller may capture biometric data associated with a monitored individual. In some examples, a monitored device may be equipped with sensors that capture biometric data from the monitored individual. Biometric data may include heart rate, body temperature, blood pressure, frequency of heart pulse waves, and/or so forth. The safety detection controller may capture the biometric data continuously, per a predetermined schedule, or in response to a triggering event. The predetermined schedule may be based on any time interval, such as one hour, 30 minutes, 15 minutes, or 5 minutes. The triggering event may correspond to an elevated measurement of biometric data that exceeds a predetermined threshold. For example, a heart rate of about 120 beats per minute or a body temperature of 100 degrees Fahrenheit may correspond to a triggering event.

At 804, the safety detection controller may analyze the biometric data to determine whether it is suggestive of an adverse health condition. In one example, the biometric data may be analyzed relative to the registered biometric profile associated with the monitored individual, and in doing so, determine whether the biometric data is typical or atypical of the individual's nominal health profile.

Additionally, or alternatively, the biometric data may be analyzed relative to a registered biometric profile of a communicable disease, and in doing so, determine whether the biometric data is typical or atypical of symptoms commonly associated with the communicable disease. The safety detection controller may select from a list of communicable diseases for analysis, based in part on those which are temporally prevalent, geographically prevalent, or both.

At 806, the safety detection controller may infer that a safety concern impacts the monitored individual based at least in part on the monitored individual's biometric data. The safety concern may be expressed as a safety score, which is intended to indicate a risk that the biometric data is associated with a communicable disease.

CONCLUSION

Although the subject matter has been described in language specific to features and methodological acts, it is to be understood that the subject matter defined in the appended claims is not necessarily limited to the specific features or acts described herein. Rather, the specific features and acts are disclosed as exemplary forms of implementing the claims.

What is claimed:

1. A system comprising:
one or more processors;
memory coupled to the one or more processors, the memory including one or more modules that are executable by the one or more processors to:
receive sensor data from a monitoring application on a first client device, wherein the sensor data is associated with a surrounding environment proximate to a first individual associated with the first client device;
retrieve dispatch event data associated with the first client device;
determine a nature of the dispatch event data;
analyze the sensor data to infer a second individual identity of a second individual proximate to the first client device; and
infer a likelihood of a safety concern impacting the first individual, based at least in part on analysis on the second individual identity and a determined nature of the dispatch event data.

2. The system of claim 1, wherein the second individual identity is associated with a second client device, and wherein the sensor data comprises an electronic handshake between the first client device and the second client device, the electronic handshake occurring unobtrusively via a wireless communication protocol, and wherein the one or more modules are further executable by the one or more processors to:
capture, from the electronic handshake, a device identifier associated with the second client device, and
wherein, to infer the second individual identity is based at least in part on the device identifier.

3. The system of claim 1, wherein the sensor data comprises at least one of video data or audio data that captures the second individual, and
wherein, to infer the second individual identity is based at least in part on analysis of the video data or the audio data.

4. The system of claim 1, wherein the one or more modules are further executable by the one or more processors to:
receive, via an oversight entity, an indication that an additional client device is proximate to the first client device, the additional client device having an additional monitoring application that monitors the surrounding environment proximate to the additional client device; and
retrieve additional sensor data from the additional monitoring application of the additional client device, and wherein, to infer the likelihood of the safety concern is further based at least in part on analysis of additional sensor data.

5. The system of claim 1, wherein the one or more modules are further executable by the one or more processors to:
transmit, to a third-party server associated with safety concerns, an inference of the second individual identity; and
receive, from the third-party server, profile data associated with the second individual identity, and
wherein, to infer the likelihood of the safety concern is further based at least in part on the profile data.

6. The system of claim 5, wherein the safety concerns relate to communicable health diseases, and
wherein, the third-party server includes a data set of individuals with known infections of one of the communicative health diseases.

7. The system of claim 5, wherein the safety concerns relate to unlawful activities, and
wherein, the third-party server includes a data set of individuals with known/suspected affiliations to unlawful activities.

8. The system of claim 1, wherein the one or more modules are further executable by the one or more processors to:
determine a geolocation associated with the first client device, based at least in part on the sensor data, and
wherein, to infer the likelihood of the safety concern impacts the first individual is further based at least in part on the geolocation.

9. The system of claim 1, wherein the dispatch event data includes real-time event data for law enforcement activities.

10. The system of claim 1, wherein the sensor data comprises real-time biometric data of the first individual, and wherein the one or more modules are further executable by the one or more processors to:
correlate the biometric data with a registered biometric profile, the registered biometric being associated with at least one of the first individual or a communicable health disease, and
wherein, to infer a likelihood of the safety concern is based at least in part on a correlation of the biometric data with the registered biometric profile.

11. The system of claim 1, wherein the one or more modules are further executable by the one or more processors to:
generate a safety score based at least in part on the likelihood of the safety score; and
in response to the safety score being greater than a predetermined safety threshold, transmit an alert message for presentation on a display of the first client device.

12. A computer-implemented method, comprising:
under control of one or more processors:
receiving sensor data from a monitoring application on a first client device, wherein the sensor data is associated with a surrounding environment proximate to a first individual associated with the first client device;
retrieving dispatch event data associated with the first client device;
determining a nature of the dispatch event data associated with the first client device;
inferring identities of one or more individuals within proximity to the first client device, based at least in part on the sensor data;
retrieving identity profiles associated with the one or more individuals; and
generating a safety score for the first individual, based at least in part on the determined nature of the dispatch event data and retrieved identity profiles.

13. The computer-implemented method of claim 12, wherein the sensor data comprises at least one of video data or audio data further comprising:
interrogating a third-party server to determine whether the identity profiles of the one or more are associated with a safety concern, the safety concern being related to one of a communicable disease or unlawful activity, and
wherein generating the safety score is further based at least in part on determining whether the identity profiles are associated with the safety concern.

14. The computer-implemented method of claim 12, wherein the dispatch event data includes real-time event data for law enforcement activities.

15. The computer-implemented method of claim 12, wherein the sensor data corresponds to real-time biometric data of a particular individual associated with the first client device, and further comprising:
analyzing the real-time biometric data to infer whether a safety concern impacts the particular individual, the safety concern relating to a physical injury, and
wherein the safety score is further based at least in part on an inference of the safety concern.

16. The computer-implemented method of claim 12, further comprising:
determining whether the safety score is greater than or equal to a predetermined safety threshold; and
transmitting an alert message to at least an oversight entity associated with the first client device, based at least in part on the safety score being greater than the predetermined safety threshold, the alert message indicating that a safety concern may impact a particular individual associated with the first client device.

17. A non-transitory computer-readable media storing computer-executable instructions that, when executed on one or more processors, cause the one or more processors to perform acts comprising:
capturing sensor data from a monitoring application on a client device, wherein the sensor data is associated with a surrounding environment proximate to a first individual associated with the client device;
retrieving dispatch event data associated with the client device;
determining a nature of the dispatch event data;
detecting one or more individuals that are within proximity to the client device, based at least in part on the sensor data;
analyzing identity profiles of the one or more individuals to determine whether a safety concern impacts a particular individual associated with the client device;
generating a safety score based at least in part on analysis of the identity profiles and a determined nature of the dispatch event data; and
in response to the safety score being greater than a predetermined safety threshold, transmitting an alert to the client device indicating a likelihood of the safety concern.

18. The non-transitory computer-readable media of claim 17, wherein the dispatch event data includes real-time event data for law enforcement activities.

19. The non-transitory computer-readable media of claim 17, wherein the sensors data corresponds to real-time biometric data of the first individual associated with the client device, and further comprising:
    retrieving historical biometric data associated with the first individual over a predetermined time interval, and
    analyzing an aggregate of the real-time biometric data and the historical biometric data to infer whether the safety concern impacts the first individual, the safety concern relating to contraction of a communicable disease, and
    wherein the safety score is further based at least in part on an inference of the safety concern.

20. The non-transitory computer-readable media of claim 17, wherein the sensor data comprises an electronic handshake between the client device and an additional client device associated with a third-party individual of the one or more individuals, and further comprising:
    capturing, from the electronic handshake, a device identifier associated with the additional client device;
    inferring an identity of the third-party individual, based at least in part on the device identifier; and
    retrieving, from a third-party server, an identity profile of the third-party individual, based at least in part on an inference of the identity.

* * * * *